United States Patent
Whitley

(10) Patent No.: US 7,449,331 B2
(45) Date of Patent: Nov. 11, 2008

(54) ROLLER BOTTLE

(76) Inventor: Kenneth W. Whitley, 9515 Meadowmont La., Raleigh, NC (US) 27615

( * ) Notice: Subject to any disclaimer, the term of this patent is extended or adjusted under 35 U.S.C. 154(b) by 317 days.

(21) Appl. No.: 10/666,357

(22) Filed: Sep. 19, 2003

(65) Prior Publication Data
US 2004/0191895 A1   Sep. 30, 2004

Related U.S. Application Data

(60) Provisional application No. 60/412,205, filed on Sep. 20, 2002.

(51) Int. Cl.
| | |
|---|---|
| *C12M 1/24* | (2006.01) |
| *C12M 3/00* | (2006.01) |
| *C12M 1/14* | (2006.01) |
| *C12M 3/04* | (2006.01) |
| *B65D 6/00* | (2006.01) |
| *B65D 90/02* | (2006.01) |

(52) U.S. Cl. .............. 435/304.1; 435/298.2; 435/299.2; 435/307.1; 435/298.1; 435/299.1; 220/669; 220/675; 220/654; 220/648; 220/672; 220/673; 215/382

(58) Field of Classification Search .............. 435/298.2, 435/304.1, 299.2, 307.1, 298.1, 299.1; 220/669, 220/675, 654, 648, 672, 673; 215/382
See application file for complete search history.

(56) References Cited

U.S. PATENT DOCUMENTS

| | | |
|---|---|---|
| D15,593 S | 12/1884 | Stickney |
| D101,984 S | 11/1936 | Fuerst |
| D144,500 S | 4/1946 | Frederics |
| 3,701,717 A | 10/1972 | Ingvorsen |
| 3,853,712 A | 12/1974 | House et al. |
| 4,717,668 A * | 1/1988 | Keilman et al. .......... 435/304.1 |
| 4,749,092 A * | 6/1988 | Sugiura et al. .............. 215/381 |
| 4,763,804 A * | 8/1988 | O'Connell .................. 215/307 |
| 4,824,787 A | 4/1989 | Serkes et al. |
| 4,912,048 A | 3/1990 | Smith et al. |
| 4,962,033 A | 10/1990 | Serkes et al. |
| 5,010,013 A | 4/1991 | Serkes et al. |
| D318,800 S | 8/1991 | Serkes et al. |
| 5,084,393 A | 1/1992 | Rogalsky |
| 5,151,366 A | 9/1992 | Serkes et al. |
| 5,256,570 A | 10/1993 | Clyde |
| 5,272,084 A | 12/1993 | O'Connell et al. |
| 5,300,438 A | 4/1994 | Augspurger et al. |
| 5,373,961 A * | 12/1994 | Harris et al. ................ 220/571 |
| 5,407,809 A | 4/1995 | Finn |
| 5,866,419 A | 2/1999 | Meder |
| 6,245,557 B1 | 6/2001 | Fouts et al. |

FOREIGN PATENT DOCUMENTS

FR   1.191.951   4/1959

* cited by examiner

*Primary Examiner*—William H. Beisner
*Assistant Examiner*—Nathan A Bowers

(57) ABSTRACT

The invention provides a roller bottle for cell growth culturing including a plurality of axial pleats therearound for increasing cell growth surface area and further including circumferential ribs integrally formed therewith for reinforcing the pleated wall structure. These circumferential ribs prevent the bottle walls from bowing outward when the inside of the bottle becomes pressurized during cell growth culturing.

16 Claims, 3 Drawing Sheets

ROLLER BOTTLE

This application claims the benefit of U.S. Provisional Application(s) No(s).: 60/412,205 Sep. 20, 2002.

BACKGROUND OF THE INVENTION

1. Field of the Invention

This invention relates to a container for cell culture production, and more particularly to a roller bottle having axial pleats for increasing cell growth surface area and circumferential ribs for reinforcing the bottle walls.

2. Description of Related Art

One type of container commonly used in the laboratory for culturing of cells is known as a "roller bottle". Roller bottles are generally cylindrically shaped and are adapted to rotate about their axes. The internal surfaces of such roller bottles are for providing active surfaces for cells. A liquid growth medium is introduced into the roller bottle. The rotating movement of the bottle keeps the internal surfaces wetted with a liquid medium, thereby encouraging the growth of cells. Rotating rollers of an appropriate apparatus are employed to rotate these roller bottles.

It is desirable to grow large amounts of cells, mostly for cell by-products, such as pharmaceutical substances that are secreted by cells. Various approaches have been used in order to increase the surface area internally of roller bottles. One approach has been to increase the amount of actual surface area available for cells to grow on.

For example, roller bottles produced as a unitary structure by a blow-molding technique are known that include longitudinal pleats formed in the walls of the roller bottle. These longitudinal pleats increase the effective surface area internally of the roller bottle. The pleats extend into the growth chamber for the purpose of increasing culture or cell yield.

It is further known to provide a culture vessel having such longitudinal pleats, and further including circumferential collars which encircle the external surface of the top and bottom end of the vessel. These collars are for the purpose of maximizing the vessel's grip point when the vessel is placed on its side on the rollers of a rotating apparatus.

The prior art also discloses a roller bottle having pleats cross-wise to the axis of the bottle for increasing the surface area for growing cells and further including at least one unpleated longitudinal drain panel, and axial reinforcing ribs along the outer edge of the cross-wise corrugation for strengthening the pleated bottle.

It is also known to use circumferential ribs on a roller bottle for the purpose of reinforcing the bottle walls. In this regard, the prior art discloses a roller bottle having flexible plastic walls and a plurality of spaced-apart circumferential reinforcement rings defined in the flexible plastic walls to cause the body to retain a generally cylindrical shape.

A problem associated with prior art roller bottles, especially those having pleats with the purpose of expanding the surface area for growing cells, has been the tendency of the bottle walls to expand when the insides of the bottles become pressurized. This causes the bottle to stop rolling on its roller rack. This is problematic because in the absence of the rotating movement, a portion of the internal surfaces becomes dry, promoting cell death in these areas.

It is desirable therefore to provide a pleated roller bottle which is reinforced so as to add rigidity to the vessel wall to prevent the bottle from expanding to the point where the roller bottle stops rolling.

SUMMARY OF THE INVENTION

The present invention provides a roller bottle for cell growth culturing including an elongate cylindrical wall having a closed bottom end and a liquid opening at an opposing top end. The elongate cylindrical wall includes a plurality of longitudinally axial extending pleats that extend from the closed end to the top end. The elongate cylindrical wall further includes circumferential ribs integrally formed therewith for reinforcing the pleated cylindrical wall.

The reinforcing circumferential ribs prevent the pleated walls from bowing outward when the inside of the bottle becomes pressurized to the point where the roller bottle stops rolling on its roller rack.

DETAILED DESCRIPTION OF THE INVENTION

Figure 1:
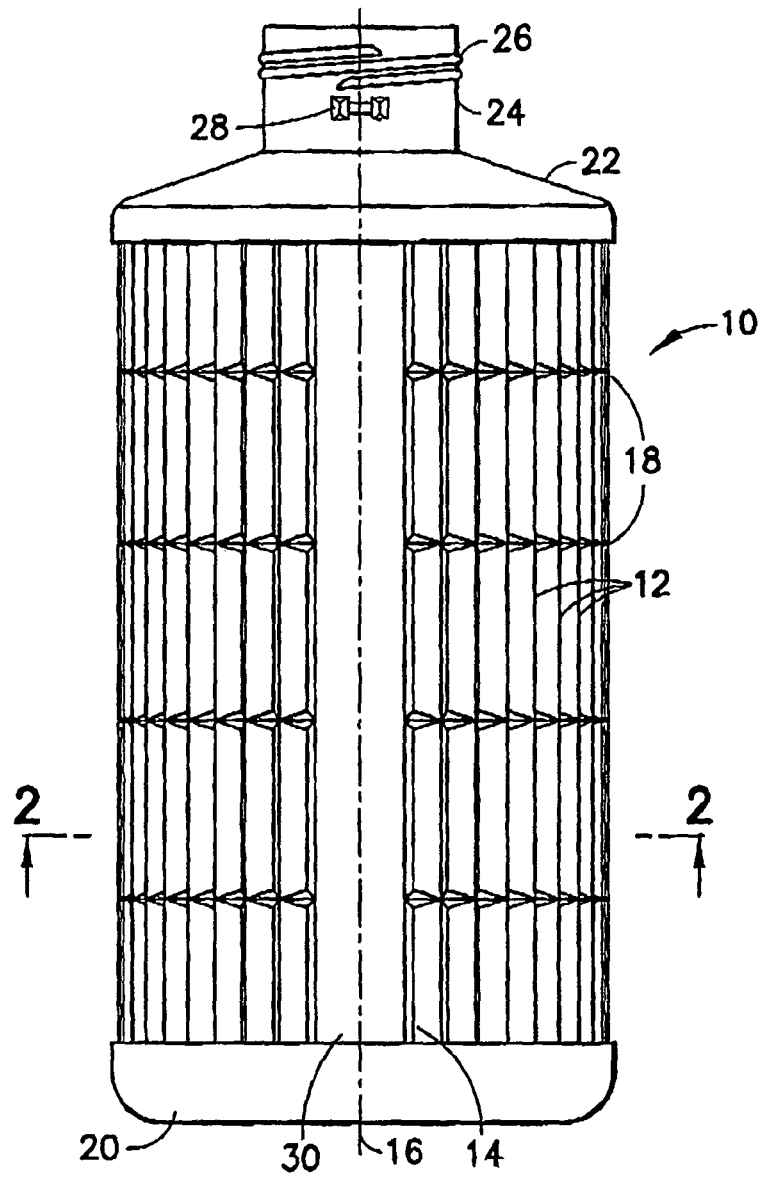
FIG. 1 is a perspective view of a roller bottle of the present invention.

Referring to the drawings in which like reference characters refer to like parts throughout the several views thereof, the roller bottle 10 of the present invention is shown. Roller bottle 10 includes a cylindrical side wall 14 which extends from a bottom wall 20 to an opposing top wall 22. Extending from top wall 22 and integral therewith is a neck portion 24 having extended screw threads 26 for receiving an internally threaded screw cap (not shown) thereon in the usual manner. Other cap connections such as bayonet connections may be used. Neck 24 may include a locking arrangement 28 for holding a cap in a locked open position on the roller bottle for maintaining the roller bottle open to the environment surrounding it.

Figure 2:
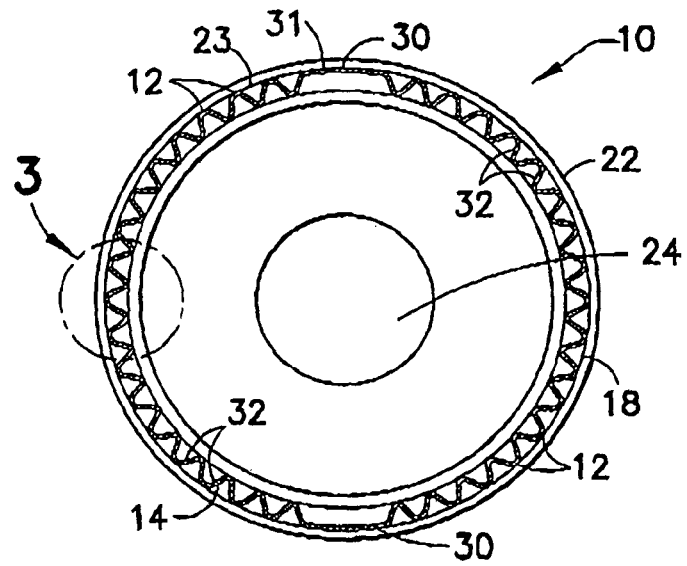
FIG. 2 is a horizontal sectional view of the device of FIG. 1 taken along lines 2-2 of FIG. 1.
Figure 3:
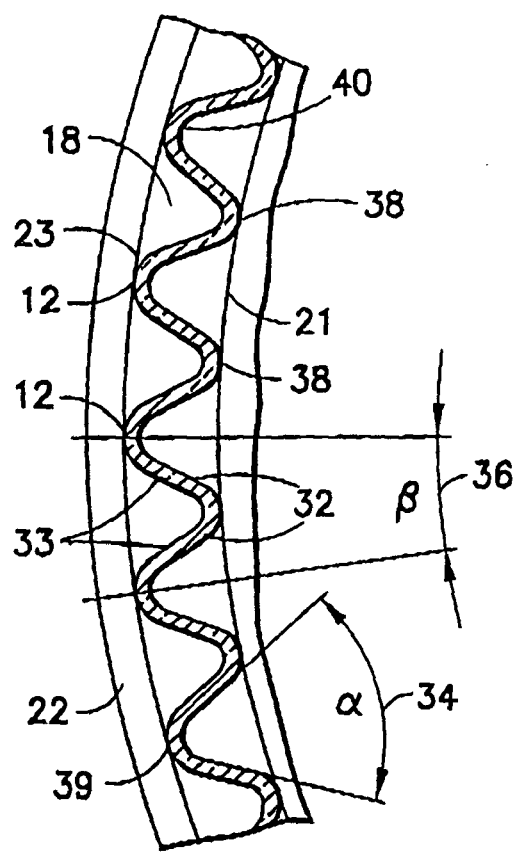
FIG. 3 is an enlarged partial sectional view of the portion of the roller bottle in FIG. 2 designated "3".

Roller bottle 10 includes longitudinal corrugations or pleats 12 extending along the side wall 14 of roller bottle 10 in the same direction as axis 16 of roller bottle 10. As can be seen in FIGS. 2 and 3, the individual pleats 12 provide a plurality of opposed facing surfaces 32 for the formation of cell growth thereon. This pleated structure increases the active surface area internally of roller bottle 10 in comparison to a conventional flat wall structure.

The pleats 12 of the inventive roller bottle are oriented parallel to axis 16 of bottle 10 so as to create grooves or channels that point toward and convey fluid to the liquid opening to make removal of cells or cell by-products easier.

While the present invention may be constructed in various sizes and configurations, the preferred structure of the present roller bottle includes a bottle which is approximately 27.08 cm (10.66 inches) in length from the top of neck 24 to the bottom of base 20. Such a configured bottle defines a growth surface area length of about 22.86 cm (9.0 inches) having a diameter of about 11.76 cm (4.63 inches). As shown in FIG. 3, the pleats forming facing internal surfaces 32 define a generally wave-like structure having outer and inner apices 38 and 40, respectively. The distance between the outer apices 38 of two pleats is approximately 0.82 cm (0.323 inches). Facing surfaces 32 of each pleat 12 define an interior angle α.

In the present embodiment, angle α 34 may be approximately 60°. Additionally, the inner apices 40 of two adjacent pleats define an interior angle β 36. In the present embodiment, angle β may be approximately 9°. It is noted that the apices 38 and 40 of pleats 12 are desirably rounded to facilitate cell adherence to the internal surface 32. Moreover, such rounded surfaces are easy to form by casing or molding and are stronger and less subjective cracking upon flexing.

As described above, a problem associated with prior art pleated roller bottles has been that the pleats tend to expand when the inside of the bottle becomes pressurized. In use, the roller bottle is sealed and warmed in an incubator. Warming raises the pressure inside the roller bottle, typically about 1 psi. The internal pressure in the roller bottle may bow the walls outward. This causes the bottle to stop rolling on the roller rack. As a result, portions of the interior surface of the bottles become dry, leading to cell death and a reduction in culture yield. The present invention solves a need by providing circumferential ribs for the purpose of adding rigidity to the pleated bottle walls, to prevent them from expanding to the point where the bottle stops rolling on the roller rack.

Figure 4:
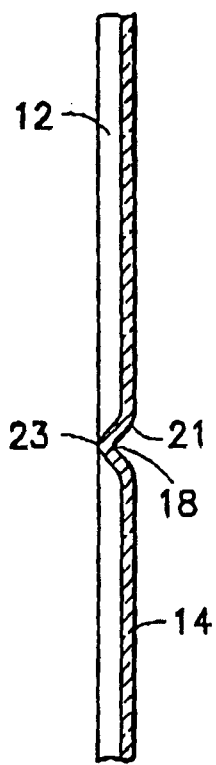
FIG. 4 is a partial sectional view of the wall of the roller bottle of FIG. 1.

Referring additionally to FIG. 4, cylindrical wall 14 of roller bottle 10 further includes circumferential ribs 18 for reinforcing cylindrical wall 14. Circumferential ribs 18 are integrally formed with cylindrical wall 14. Circumferential ribs 18 define tension members that prevent the roller bottle from expanding outward in a response to internal pressure in the roller bottle.

As shown in FIG. 3, it is noted that in a preferred embodiment, inner wall 21 of rib 18 is flush with apex 38 of pleats 12 on internal surface 32 of roller bottle 10. In a further preferred embodiment, outer wall 23 of rib 18 is flush with apex 39 of pleats 12 on external surface 33 of roller bottle 10. With reference to FIG. 2, it is particularly desired that outer wall 23 of rib 18 is flush with outer wall 31 of the planar sections 30 to facilitate the conveyance of fluid to the liquid opening along panels 30 and eliminate the possibility that the liquid contents of the bottle would become trapped in these areas.

Figure 5:
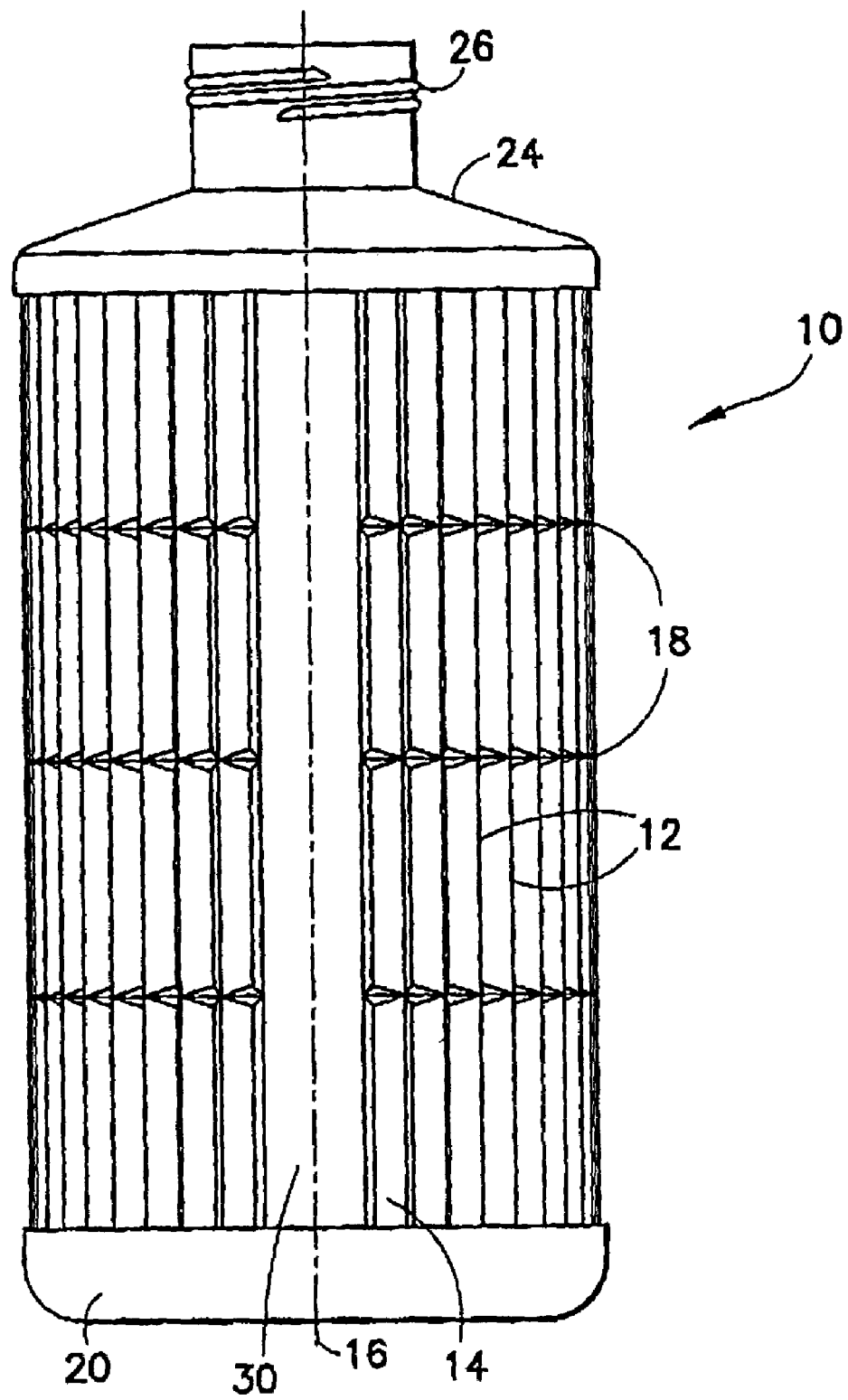
FIG. 5 is a perspective view of a roller bottle of the present invention.

In the embodiment of the invention shown in FIG. 1, four longitudinally spaced ribs are shown. However, it is contemplated that the bottle may include from two to ten circumferential ribs for reinforcement, preferably 3-6 evenly spaced ribs along the length of the roller bottle. Most preferably, the roller bottle of the invention includes three evenly spaced ribs along the length of the bottle, as shown in FIG. 5. However, the invention is not limited to this particular number of reinforcing ribs. It is noted that extra circumferential ribs can be concentrated in the area needing the most reinforcement.

The number of ribs provided is selected to maximize strength, while minimizing the loss of surface area and for cell growth. For example, it has been found by the present inventor that the internal surface area of an approximately 1700 square centimeter (sq. cm.) roller bottle is 1,734 sq. cm. in the absence of radial ribs 18, as compared to 1,694 sq. cm.

As shown in FIGS. 1-2, roller bottle 10 may further include diametrically opposed longitudinally extending planar sections 30 where no pleats 12 are present in order to enhance the microscopic viewing of the contents of roller bottle 10 and/or to facilitate the formation thereof. In preferred embodiments of the present invention, the roller bottle contains two diametrically opposed planar sections 30 to facilitate microscopic viewing. The particular arrangement of planar sections 30 shown in the drawings is not critical. Moreover, the width of planar sections 30 is not critical, expect that these panels also represent a loss of increase surface area. A problem associated with prior art pleated roller bottles having planar sections for microscopic viewing has been that these sections become distorted when the inside of the bottle becomes pressurized, making microscopic viewing difficult. It is noted that reinforcing ribs 18 of the inventive roller bottle further serve to prevent this distortion of the planar sections to allow for continued microscopic viewing.

It is noted that roller bottle 10 may include a recessed portion (not shown) at bottom wall 20 to facilitate stacking of the roller bottle with a similar bottle in a nesting relationship.

The present invention provides a longitudinally pleated roller bottle which can be used to increase the culture or cell yields per unit for either adherent-type cells or cells that grow in suspension. It is noted that adherent-type cells include cells which require a support surface to grow on, as well as cells capable of growing on a support surface. By the phrase "increase in culture or cell yields", it is meant that there is an increase in the number of cells and/or their by-products per culture vessel or unit. As shown in the drawings herein, the cylindrical wall of the body portion of the roller bottle is longitudinally pleated along a substantial portion of its length, thus corrugating the interior and exterior surfaces of the body wall in the vessel. The interior corrugating increases the surface area available for the attachment and growth of adherent-type cells, thus increasing the culture or cell yields per vessel. Moreover, it is noted that with respect to the cells which grow in suspension, the interior corrugating of the inventive roller bottle enhances agitation of the suspension culture and helps disperse the cells and promote growth of the culture.

After cells have formed on internal surfaces of the roller bottle of the present invention by rolling in the proper environment for the formation of the cells, the roller bottle with formed cells on the walls thereof is removed from the conventional roller bottle apparatus. The cell forming liquid media remaining in the bottle may be decanted from the bottle along the longitudinal pleats and flat viewing panels and a small amount of saline solution may be added to prevent the cells from drying. Alternatively, the liquid media may remain if it is only a small amount. Thereafter, a scraper apparatus may be used for removing cells from the internal surface of the roller bottle.

A more conventional procedure for removing cells is the introduction of a solution containing the proteolytic enzyme trypsin, together with a chelating agent, which has the effect of causing the cells to release from the internal surface for decanting from the roller bottle along the longitudinal pleats and longitudinal planar sections. Subsequently, the bottle is generally discarded. Thus, the advantage of providing a roller bottle, such as that of the present invention, which may be inexpensively produced by blow-molding, used once and discarded is readily apparent. The inventive roller bottle provides a unitary structure including an elongate cylindrical wall with a greatly increased surface area for cell growth formation therein, these cylindrical walls further including reinforcing ribs therearound and integrally formed therewith for the purpose of reinforcing the bottle walls. These reinforcing ribs eliminate the need to discard the roller bottle prematurely during culturing due to repeated flexing of the pleats which can cause fatigue and cause the bottle to stop rolling on the roller bottle apparatus, especially during long periods of use during the cell culturing batch process. The reinforcing radial ribs prevent the bending and extension of the longitudinal pleats.

In viewing generally the conditions for producing roller bottles in accordance with the invention, a variety of thermoplastic materials may be utilized including, for example polystyrene, polyethylene terephthalate, the polyolefins and polyvinyl chloride. Polystyrene is particularly desirable as cells appear to grow well and in large numbers on this material.

The wall of the bottle should have a sufficient thickness to provide a bottle with adequate strength when filled with liquid medium. Typically, the film thickness will be from 1-60 thousandths of an inch for a 2.25 liter roller bottle. The thermoplastic resin used for forming bottles by extrusion, blow or injection blow-molding techniques should be able to readily flow to form the longitudinal pleats and reinforcing circumferential ribs of the bottle.

It is noted that only preferred embodiments of the invention have been described and that numerous substitutions, modifications and alterations are permissible without departing from the spirit and scope of the invention.

What is claimed is:

1. A container for cell growth culturing comprising:
an elongate cylindrical wall having a closed bottom end and a liquid opening at an opposing top end, said elongate cylindrical wall including (i) a plurality of longitudinally axial extending pleats that at least partially extend from said closed end to said top end, each said pleat including a first side wall extending between a first end point and a first apex; and a second side wall extending between a second end point and said first apex, said first apex being located radially further from a longitudinal center of said container than said first and second end points; (ii) at least one circumferential rib integrally formed with said cylindrical wall for reinforcing said cylindrical wall, wherein said rib includes an outer wall extending radially outwardly from, and continuously between, said side walls of each of said pleats, said rib being superimposed across said pleats, said rib outer wall being flush with outermost portions of said first apices of said pleats such that said rib outer wall does not protrude radially outwardly from said first apices; and (iii) at least one unpleated longitudinal section defining a drain panel, said rib not being superimposed across said drain panel and said rib outer wall being flush with the outermost portions of said drain panel such that said rib outer wall does not protrude radially outwardly from said drain panel.

2. The container of claim 1, wherein the container is a roller bottle.

3. The container of claim 1, wherein said cylindrical wall includes two diametrically opposed unpleated longitudinal sections, each defining a drain panel.

4. The container of claim 1, wherein extending from said top end is a neck portion having integral external screw threads for receiving an internally screw threaded cap thereon.

5. The container of claim 4, wherein said neck portion further includes a locking arrangement for holding a cap in a locked open position on said container for maintaining said container open to an environment surrounding said container.

6. The container of claim 1, wherein said pleats define a plurality of opposed facing internal surfaces for the formation of cell growth thereon.

7. The container of claim 1, wherein said first and second side walls are convergently disposed relative to said first apex.

8. The container of claim 1, wherein said first and second side walls define an angle of about 60 degrees therebetween.

9. The container of claim 1, wherein a juncture is defined between adjacent said pleats with said second end point of a first said pleat being connected to said first end point of a second said pleat, said juncture defining a second apex.

10. The container of claim 1, wherein said first apices of two adjacent said pleats are separated by an angle of about 9 degrees.

11. The container of claim 1, at least a portion of said first apices being rounded.

12. The container of claim 9, wherein said second apices of two adjacent said pleats are separated by a distance in the range of about 0.80 cm. to about 0.85 cm.

13. The container of claim 9, at least a portion of said second apices being rounded.

14. The container of claim 9, wherein said rib includes an inner wall that extends radially inwardly from said pleats, said rib inner wall being flush with innermost portions of said second apices of said pleats.

15. The container of claim 1, wherein said container includes three ribs.

16. The container of claim 1, wherein said container includes four ribs.

* * * * *